United States Patent
Bethers et al.

(10) Patent No.: US 11,597,713 B2
(45) Date of Patent: Mar. 7, 2023

(54) METHOD FOR PURIFYING CRYSTALS USING SOLVENT VAPORS

(71) Applicants: Pratt Bethers, Arvada, CO (US); David Goodman, III, Federal Heights, CO (US)

(72) Inventors: Pratt Bethers, Arvada, CO (US); David Goodman, III, Federal Heights, CO (US)

( * ) Notice: Subject to any disclaimer, the term of this patent is extended or adjusted under 35 U.S.C. 154(b) by 185 days.

(21) Appl. No.: 17/081,131

(22) Filed: Oct. 27, 2020

(65) Prior Publication Data
US 2021/0107884 A1 Apr. 15, 2021

Related U.S. Application Data

(63) Continuation of application No. 16/025,967, filed on Jul. 2, 2018, now Pat. No. 10,851,076.

(60) Provisional application No. 62/543,792, filed on Aug. 10, 2017.

(51) Int. Cl.
*C07D 311/80* (2006.01)
*B01D 9/00* (2006.01)

(52) U.S. Cl.
CPC ............ *C07D 311/80* (2013.01); *B01D 9/005* (2013.01); *B01D 9/0036* (2013.01); *B01D 2009/0086* (2013.01); *C07B 2200/13* (2013.01)

(58) Field of Classification Search
CPC .... C07D 311/80; B01D 9/0036; B01D 9/005; B01D 2009/0086; B01D 9/0059; C07B 2200/13
See application file for complete search history.

(56) References Cited

U.S. PATENT DOCUMENTS

| | | | |
|---|---|---|---|
| 7,700,368 B2 | 4/2010 | Flockhart et al. | |
| 8,884,020 B2 | 11/2014 | Talley et al. | |
| 9,186,386 B2 | 11/2015 | Speier | |
| 9,512,118 B2 | 12/2016 | Yamamoto | |
| 9,765,000 B2 | 9/2017 | Nadal Roura | |
| 9,879,292 B2 | 1/2018 | Winnicki et al. | |
| 10,851,076 B2 * | 12/2020 | Bethers | B01D 9/005 |
| 2017/0008870 A1 | 1/2017 | Dibble et al. | |
| 2018/0344785 A1 | 12/2018 | Robertson | |

OTHER PUBLICATIONS

Canadian Office Action dated Aug. 20, 2021 issued in corresponding CA Appln. No. 3,048,396.
Canadian Office Action issued in correpsonding application CA 3,048,396 dated May 12, 2021 (4 pages).

* cited by examiner

*Primary Examiner* — John M Mauro
(74) *Attorney, Agent, or Firm* — Carter, DeLuca & Farrell LLP

(57) ABSTRACT

A Reflux Rinsing method for purifying crystals using solvent vapor through dynamic equilibrium recrystallization. Feed material having tetrahydrocannabinol acid (THCA) is inserted into a reaction vessel having walls, and upper portion, and a lower portion with a bottom surface. The feed material is exposed to a hydrocarbon liquid in the reaction vessel in a quantity sufficient to keep liquid present in equilibrium with gas in the reaction vessel through the recrystallization process, forming a raw extract having THCA. The walls and bottom surface of the reaction vessel are coated with raw extract. The reaction vessel is heated and then the heating is discontinued. Vapor/thin-film DER is promoted in the reaction vessel for a predetermined length of time with no solvent reflux, resulting in formation of purified crystals of THCA under pressure. The hydrocarbon solvent is reclaimed from the reaction vessel, leaving the purified crystals and impurities. When the reaction vessel is opened, the purified crystals and impurities are removed.

16 Claims, 17 Drawing Sheets

METHOD FOR PURIFYING CRYSTALS USING SOLVENT VAPORS

CROSS-REFERENCE PARAGRAPH

The present application is a continuation of U.S. patent application Ser. No. 16/025,967 filed on Jul. 2, 2018 which claims priority to U.S. Provisional Patent Application No. 62/543,792, filed Aug. 10, 2017. The entire contents of all of which are incorporated by reference herein.

FIELD OF THE INVENTION

This invention relates to a method for purifying crystals and, more particularly, to a method for purifying crystals using solvent vapor through dynamic equilibrium recrystallization (DER).

BACKGROUND OF THE INVENTION

*Cannabis*, more commonly known as marijuana, is a genus of flowering plants that includes at least three species: *Cannabis sativa, Cannabis indica*, and *Cannabis ruderalis* as determined by plant phenotypes and secondary metabolite profiles.

The use of *cannabis* for social and medical purposes has been known for almost of all humanity's recorded history. *Cannabis* is most commonly administered via inhalation or consumption of marijuana-infused food and drink. However, since 1972 marijuana has been classified as a Schedule I drug under the U.S. Controlled Substances Act because the U.S. federal government considers it to have "no accepted medical use." In stark contrast to this position, a number of U.S. states and the District of Columbia have recognized the medical benefits of *cannabis* and have decriminalized its medical use.

In 2014, the U.S. Attorney General Eric Holder announced that the federal government would allow states to create a regime that would regulate and implement the legalization of *cannabis*, including loosening banking restrictions for *cannabis* dispensaries and growers.

The U.S. government has set a precedent for patenting *cannabis*, and *cannabis*-related inventions. For example, U.S. Pat. No. 6,630,507 issued on Oct. 7, 2003 and assigned on the patent face to The United States of America, is directed to methods of treating diseases caused by oxidative stress by administering therapeutically effective amounts of a cannabidiol (CBD) cannabinoid from *cannabis* that has substantially no binding to the N-methyl-D-aspartate (NMDA) receptor, wherein the CBD acts as an antioxidant and neuroprotectant. A search of the USPTO Patent Application Information Retrieval (PAIR) system reveals the existence of thousands of *cannabis* related applications and issued patents.

Despite the official position of the U.S. federal government, and as recognized by the states that have legalized it, *cannabis* has been shown to provide substantial benefits for medical and recreational uses. *Cannabis* is regularly used by a wide cross-section of society to treat a variety of maladies, conditions and symptoms including, but not limited to: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

Cannabinoids are terpenophenolic compounds found in *Cannabis sativa*, an annual plant belonging to the cannabaceae family. The plant contains more than 400 chemicals and approximately 70 cannabinoids. The latter accumulate mainly in the glandular trichomes. The most active of the naturally occurring cannabinoids is tetrahydrocannabinol (THC), which is used for treating a wide range of the aforementioned medical conditions.

Cannabidiol (CBD), an isomer of THC, is a potent antioxidant and anti-inflammatory compound known to provide protection against acute and chronic neuro-degeneration; cannabigerol (CBG), found in high concentrations in hemp, which acts as a high affinity; and cannabichromene (CBC), which possesses anti-inflammatory, anti-fungal and antiviral properties. Many phytocannabinoids have therapeutic potential in a variety of diseases and may play a relevant role in plant defense as well as in pharmacology. Accordingly, biotechnological production of cannabinoids and cannabinoid-like compounds with therapeutic properties is of utmost importance. Thus, cannabinoids are considered to be promising agents for their beneficial effects in the treatment of various diseases.

One method of cannabinoid preservation includes separating a cannabinoid ethanol (EtOH) mixture from a *cannabis* extract through a filtration process, forming a slurry by combining a crystalline compound with the cannabinoid EtOH mixture, and heating and agitating the slurry in a pressurized chamber to form a colloidal cannabinoid EtOH mixture.

The colloidal cannabinoid EtOH mixture is distributed into a tray to form an evenly distributed mixture layer. An evaporation vessel is formed for the evenly distributed mixture layer through the attachment of a detachable cover to the tray, and the evaporation vessel is positioned and heated within a heating chamber. A rapid cooling process is performed as the evenly distributed mixture layer approaches saturation temperature, and this process is repeated until crystal formation is detected within the evenly distributed mixture layer. The evaporation vessel is removed from the heating chamber upon detection of crystal formation.

Recrystallizations of cannabinoids from solvents, in particular from non-polar hydrocarbon solvents, are well known in the art. These processes represent a classic recrystallization, where the solvent is heated to increase solubility of the compound to be recrystallized and then cooled, creating a supersaturated solution that grows crystals.

Other recrystallization processes include using a second, weak solvent that, when added to the saturated solvent, causes precipitation of crystals. Still other, less common recrystallization techniques exist for specialized crystal growth, such as those made for protein crystallography where a reactant is added to the solvent, producing a compound as it crystallizes.

In all cases, crystal growth is limited by the ability of the molecule to move into regularly ordered, crystalline structures while excluding impurities, without re-dissolving the growing crystals. If heat is applied, the solubility of the compound increases in the solvent and crystallization is limited. Kinetic energy as vibration can be applied, short of heating the solution, to provide kinetic energy for mass transfer without heat. Electrical potentials have been applied to crystal growth, enhancing the process under controlled conditions.

These processes rely on successive recrystallization passes that break down or destroy the previous crystal, release included impurities, and grow a new crystal that is more pure due to dilution of impurities in the solvent during the destruction phase. Crystal manufacturing processes prefer growing by deposition of new material, not purification by rearrangement because their process involves growth, destruction and regrowth. Time for growth has been the limiting factor in performing the recrystallization methods.

DESCRIPTION OF RELATED ART

U.S. Pat. No. 7,700,368 issued to Flockhart, et al., on Apr. 20, 2010 for METHODS OF PURIFYING CANNABINOIDS FROM PLANT MATERIAL discloses methods of preparing cannabinoids in substantially pure form starting from plant material. Also described are substantially pure preparations of various cannabinoids and cannabinoid acids, and also extracts enriched in cannabinoids and cannabinoid acids.

U.S. Pat. No. 8,884,020 issued to Talley, et al., on Nov. 11, 2014 for INDOLE COMPOUNDS discloses indole derivatives that are useful for treating pain, inflammation and other conditions. Certain of the compounds are benzyl derivatives and others are benzoyl derivatives. The compounds are substituted at least at the 3 position of the indole.

U.S. Pat. No. 9,186,386 issued to Speier, on Nov. 17, 2015 for PHARMACEUTICAL COMPOSITION AND METHOD OF MANUFACTURING discloses methods of obtaining an extract of *cannabis* plant material as well as subsequent processing of the extract to provide a concentrate of *cannabis*. Also described are pharmaceutical dosage forms (e.g., oral thin films and transdermal patches) that include the concentrate (or extract) of *cannabis*, as well as methods of medical treatment that include administering the pharmaceutical dosage forms.

U.S. Pat. No. 9,512,118 issued to Yamamoto, on Dec. 6, 2016 for CRYSTAL OF FUSED HETEROCYCLIC COMPOUND discloses a crystal of 1-ethyl-7-methyl-3-{4-[(3-methyl-3H-imidazo[4,5-b]pyridin-2-yl)oxy]phenyl-}-1,3-dihydro-2H-imidazo[4,5-b]pyridin-2-one useful as a prophylactic or therapeutic agent for schizophrenia and the like, which shows an X-ray powder diffraction pattern having characteristic peaks at interplanar spacings (d) of 13.59 plus or minus 0.2 and 6.76 plus or minus 0.2 Angstroms in powder X-ray diffraction.

U.S. Pat. No. 9,765,000 issued to Nadal Roura, on Sep. 19, 2017 for METHODS OF PURIFYING CANNABINOIDS, COMPOSITIONS AND KITS THEREOF discloses methods of purifying one or more cannabinoids from a plant material, purified cannabinoids and pharmaceutical compositions comprising one or more cannabinoids produced by the disclosed method, methods and uses for treating a disease or condition employing such purified cannabinoids and pharmaceutical compositions.

U.S. Pat. No. 9,879,292 issued to Winnicki, et al., on Jan. 30, 2018 for APPARATUS AND METHODS FOR BIOSYNTHETIC PRODUCTION OF CANNABINOIDS discloses an apparatus and methods for producing tetrahydrocannabinolic acid (THCA), cannabichromenic acid (CBCA) and cannabichromenic acid (CBCA) in different ratios. The apparatus comprises: (i) a bioreactor comprising (a) an automated supply system configured to deliver a first automated supply of cannabigerolic acid (CBGA), a cannabinoid acid synthase, and a reaction mixture; and (b) a second automated system to cease the reaction; (ii) a controller configured to modify a property of the reaction mixture to produce the desired products; and (iii) an extractor configured to recover the tetrahydrocannabinolic acid (THCA), cannabichromenic acid (CBCA) or cannabidiolic acid (CBDA) and cannabichromenic acid.

SUMMARY OF THE INVENTION

While recrystallization from a super-saturated solution is well understood, the present invention allows crystal rearrangement and purification to take place in the vapor and/or liquid film covering the crystals. Mass transfer takes place at the interface of the vapor/liquid film on the crystals, allowing the molecules to rearrange and purify, while the impurities flow down the vessel by gravity. In the present invention, crystals purify by rearrangement, not by growth in mass, allowing for a single recrystallization pass as opposed to convention, sequential recrystallizations, each taking three to seven days. Moreover, traditional recrystallization suffers from losses of the starting crystal to the solvent that is not recrystallized at each step, which can be recovered later but represent an "apparent loss" during a single recrystallization cycle that accumulates during multiple recrystallization steps.

Compounds dissolve into solution, but solvents can also dissolve onto crystals, much like desiccants attract and hold water. Strong desiccants can hydrate to point of a thin film of water covers the mass. This is also true of other solvent vapors that are strongly attracted to solids, such as butane attracted to cannabinoids, essential oils, and other plant components. The extract mass becomes "wet" in the atmosphere of saturated hydrocarbon vapors, and the impurities (essential oils, neutral cannabinoids, etc.) are more strongly attracted to a hydrocarbon solvent than the acid forms of the cannabinoids. This allows the impurities to attract more solvent, become wetter, and flow down the sides of the vessel while allowing the cannabinoid acid form molecules to be incorporated into the rearranging crystals as they increase in purity. Neutral forms of cannabinoids are more soluble and are drained away from the crystal with the other more soluble impurities.

This is not the same as washing the crystals with butane liquid formed within a vessel by reflux (i.e., evaporating the solvent in a hot zone and re-condensing the solvent in a cool zone above the crystals to allow the fresh solvent to wash the surface of the crystals). The solvent reflux method of the present invention removes impurities from the surface of crystals from the previous recrystallization, but does not facilitate mass transfer and purification through dynamic equilibrium recrystallization. Reflux is a process driven by evaporation and condensation.

The reflux process can provide enough solvent to dissolve the crystals entirely and wash them down the surface of the vessel. Such a method does not allow for the time for crystal growth afforded by a resident thin-layer of vapor deposited solvent. The degree of solvent film on the surface of the crystal, and the slope of vessel wall for impurity draining from the crystalline mass must be controlled to allow the crystals time to purify through recrystallization, but not re-dissolve them in solvent or wet the crystals enough to wash them down the vessel.

As seen with live resin extraction runs, the high levels of terpenes in the extract pull additional hydrocarbon solvent into the crystalline mass so strongly that the increase in solvent in the mass rinses it down the wall of the vessel. As the impurities increase in the flow of solvent down the mass, the solution pulls in additional solvent, making it thinner and improving the flow. Butane liquid flowing down is replaced by solvent vapors in equilibrium on the surface of the fresh crystal. This process is driven by solubility, not evaporation and condensation.

Once the surface film of solvent is deposited onto the crystal molecules from the crystal dissolve, and the layer of solvent becomes saturated. The layer is not flushed away as in a reflux rinsing method, but stationary so that dynamic equilibrium results, where molecules and impurities can leave the crystal into the solvent, and molecules can come back onto the crystal, allowing for crystal purification without increases in mass as in other recrystallization methods. If an excess of solvent is used, the crystal dissolves into the solvent and is rinsed away without residence time for dynamic equilibrium recrystallization purification.

In accordance with the present invention, there is provided a method for purifying crystals using solvent vapor through dynamic equilibrium recrystallization (DER). Feed material having tetrahydrocannabinol acid (THCA) is inserted into a reaction vessel having walls, and upper portion, and a lower portion with a bottom surface. The feed material is exposed to a hydrocarbon liquid in the reaction vessel in a quantity sufficient to keep liquid present in equilibrium with gas in the reaction vessel through the recrystallization process, forming a raw extract having THCA. The walls and bottom surface of the reaction vessel are coated with raw extract. The reaction vessel is heated and then the heating is discontinued. Vapor/thin-film DER is promoted in the reaction vessel for a predetermined length of time with no solvent reflux, resulting in formation of purified crystals of THCA under pressure. The hydrocarbon solvent is reclaimed from the reaction vessel, leaving the purified crystals and impurities. When the reaction vessel is opened, the purified crystals and impurities are removed.

It is therefore an object of the invention to provide a method for purifying crystals.

It is a further object of the present invention to provide a method for purifying crystals that uses solvent vapor in a recrystallization process.

It is a further object of the present invention to provide a method for purifying crystals using heat to drive vapors and reflux rinsing to remove impurities at the surface of an impure crystalline mass, leaving purified crystals and impurities in a reaction or collection vessel.

It is a further object of the present invention to provide a method for purifying crystals that can be scraped from the sides of a reaction or collection vessel.

These and other objects and advantages of the present invention are more readily apparent with reference to the following detailed description and the accompanying drawings.

BRIEF DESCRIPTION OF THE DRAWINGS

A complete understanding of the present invention may be obtained by reference to the accompanying drawings, when considered in conjunction with the subsequent detailed description, in which.

Like reference numerals refer to like parts throughout the several views of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

The Reflux Rinsing method for purifying crystals of the present invention uses solvent vapor through dynamic equilibrium recrystallization. A pressure vessel contains a liquefied gas solvent, impure crystalline starting material initially, and a purified crystalline mass at the conclusion of the purifying process. A mechanism is provided for providing pressure to contents of the pressure vessel and for heating the lower portion thereof. A timer is also connected to the mechanism, the timer being set to heat the pressure vessel to drive vapors and reflux rinsing to remove impurities at the surface of an impure crystalline mass, to reclaim the solvent, leaving purified crystals and impurities in the pressure vessel, and to open the pressure vessel to remove the purified crystals from the vessel walls and bottom surface and to remove the impurities from the vessel.

Figure 1:
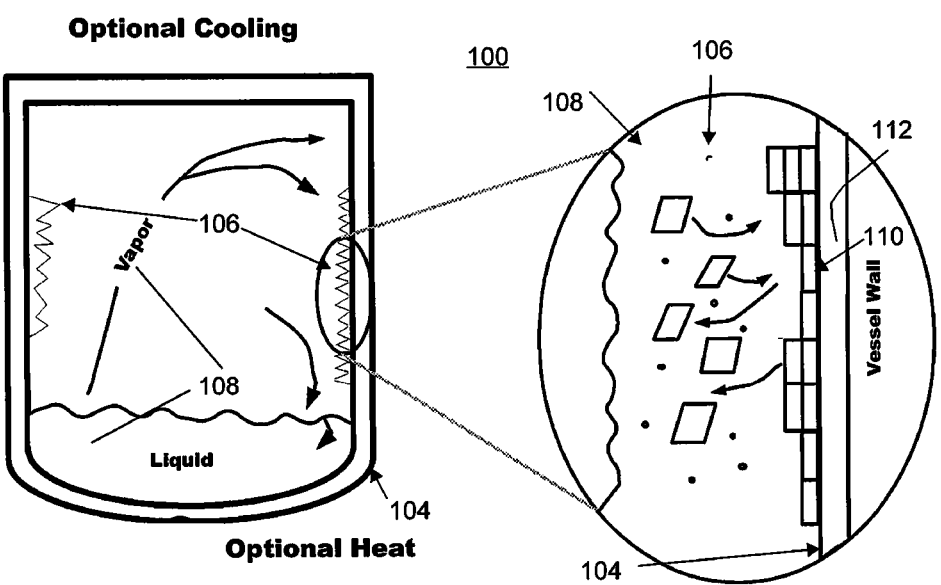
FIG. 1 is a diagram of thin-film/vapor recrystallization in accordance with the present invention.

Referring now to FIG. 1, a diagram of thin-film/vapor recrystallization apparatus 100 is shown for purifying crystals in an initial crystalline mass 106 using solvent vapor through dynamic equilibrium recrystallization (DER). The recrystallization at the surface of the crystals in the thin film is provided in a butane vapor (gas)-saturated vessel 102.

A pressure vessel 104 is provided, into which is placed impure crystalline starting material 106, portions of crystallized biological plants in the preferred embodiment.

Liquified gas solvent 108 is introduced into pressure vessel 104.

Purified crystalline mass 110 with impurities is provided. The impurities are removed and crystal reforms, while impurities increase in the solvent layer, pulling more solvent 108, and becoming less viscous to flow down the walls 112 of vessel 104, not by vapor pressure, but by solubility. Solvent 108 with impurities running down walls 112 is replaced by vapor condensation on the new, purified crystal surface.

Figure 2:
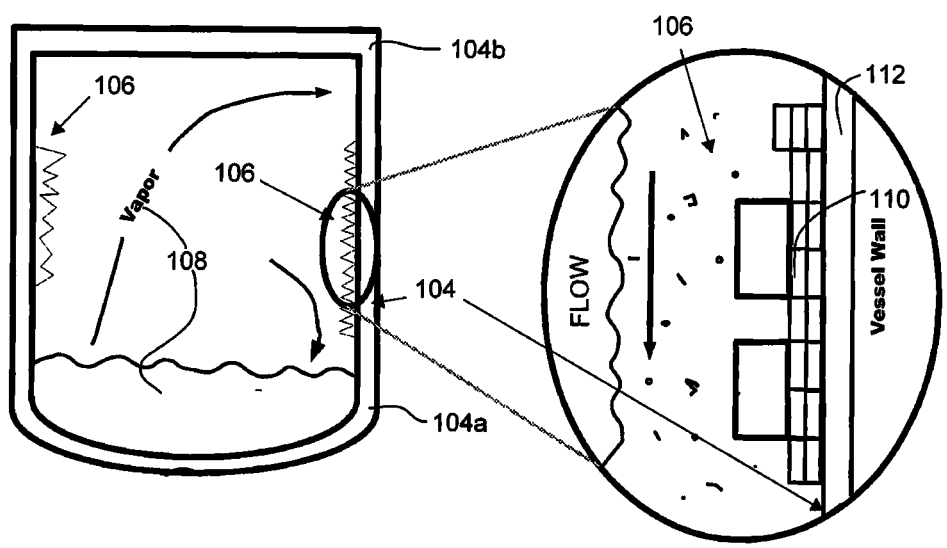
FIG. 2 is a diagram of Reflux Rinsing.

Referring now to FIG. 2, a process known as Reflux Rinsing is performed, using a thin film of solvent 108 flowing over crystalline mass 106. This solvent 108 is the result of reflux action that heats the bottom 104*a* of vessel 104, so vapors rise to the top 104*b* thereof, where they condense into a film. This film flows over the crystalline mass 106 as in the DER hereinabove described. The driving force is reflux and the cycle time for rinsing is short, so as not to redissolve the crystals in a continuous stream of fresh reflux solvent 108 and recombine with the impurities at the bottom 104*a* of vessel 104. This process can be combined with the DER process to control the balance between recrystallization and rinsing the surface of purified crystalline mass 110.

In the Reflux Rinsing procedure, pressure vessel 104 is provided for containing crystalline starting material with surface impurities 106, liquefied gas solvent 108, and vapor. A film of liquid is permitted to flow over crystalline mass 106, rinsing off the surface thereof. The crystal or purified crystalline mass 110 is then spread on the surfaces of pressure vessel 104.

Figure 3:
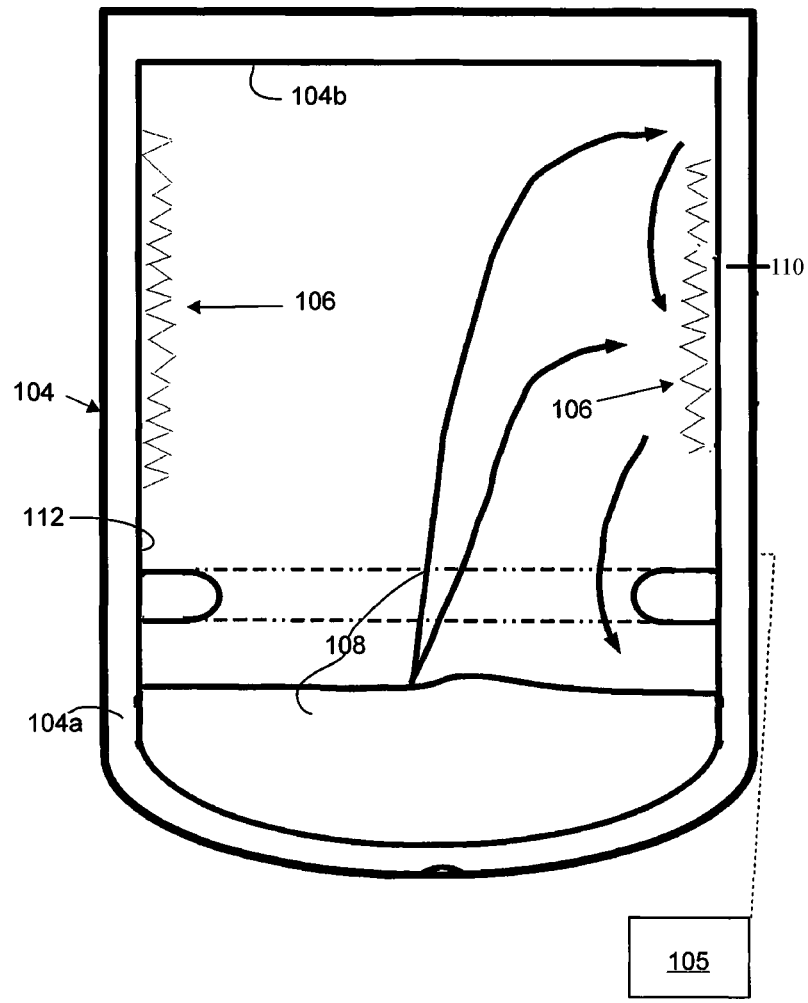
FIG. 3 is a combination of Reflux Rinsing and DER.

Referring now to FIG. 3, there is shown a combination process. DER and Reflux Rinsing processes are combined in the overall process to optimize crystal purity and yield. Once again, pressure vessel 104 is loaded with impure crystalline starting material 106. Liquefied gas solvent 108 is then introduced into pressure vessel 104, forming solvent vapor. A thin film of liquid flows over purified crystalline mass 110, rinsing off the surface thereof.

The steps in the Reflux Rinsing method are:

a) applying the initial, impure purified crystalline mass 106 to walls 112 of pressure vessel 104;

b) adding hydrocarbon liquid to pressure vessel 104, enough to keep liquid present in equilibrium with the gas through the recrystallization process; and c) initially heating the bottom 104a of pressure vessel 104 to drive vapors to the top 104b thereof, where they condense on the cooler surface and rinse the surface of a purified crystalline mass 110 using reflux.

Following a brief period of initial reflux rinsing controlled by a timing mechanism 105, vapor/thin-film DER is promoted in pressure vessel 104 for hours at a constant temperature with no solvent reflux. The Reflux Rinsing process then continues:

d) gently heating the bottom 104a of pressure vessel 104 again to drive vapors and reflux rinsing to remove the final impurities that have migrated to, or accumulated at, the surface of purified crystalline mass 110;

e) cycling step (d) with control over temperature, pressure, and other variables as necessary to maximize crystal yield and purity;

f) reclaiming the hydrocarbon solvent 108, leaving the crystals and impurities in pressure vessel 104; and g) opening pressure vessel 104, removing the purified crystals 110 from the walls 112 thereof and the impurities (i.e., other cannabinoids, essential oils, etc.) from the bottom 104a of pressure vessel 104.

Referring now to FIGS. 4-8, a Reflux Rinsing apparatus 400 is provided for performing the Reflux Rinsing process controls temperature, pressure, surface area of crystallization, angle of interior surfaces to control flow velocity, length of the path of crystallization relative to the surface area, thickness of purified crystalline mass 110, and the pressure/vapor density of the liquid/vapor solvent 108.

Reflux Rinsing apparatus 400 is sealed, with the ability to Reflux Rinse and DER with a temperature control zone at the bottom 402 thereof, and a temperature control zone 404 at the top thereof for rapid refluxing, or merely to heat bottom 402 of apparatus 400 and allow the cooler top 404 to condense vapors over time. Reflux Rinsing apparatus 400 can switch between Reflux Rinsing and DER sequentially, as necessary.

A key component of any apparatus used for the Reflux Rinsing process is creating surface area for crystal growth to occur. Thus, any mechanism by which surface area is increased within vessel 104 is considered within the scope of the invention.

Moreover, since the force of gravity and the angle of vessel walls 112 also affect crystal growth and overall process time, increasing force at the walls 112 of vessel 104 through use of a centrifuge or any other method of adjusting force, and changing the angle of vessel walls 112 is considered within the scope of the invention.

Figure 4:
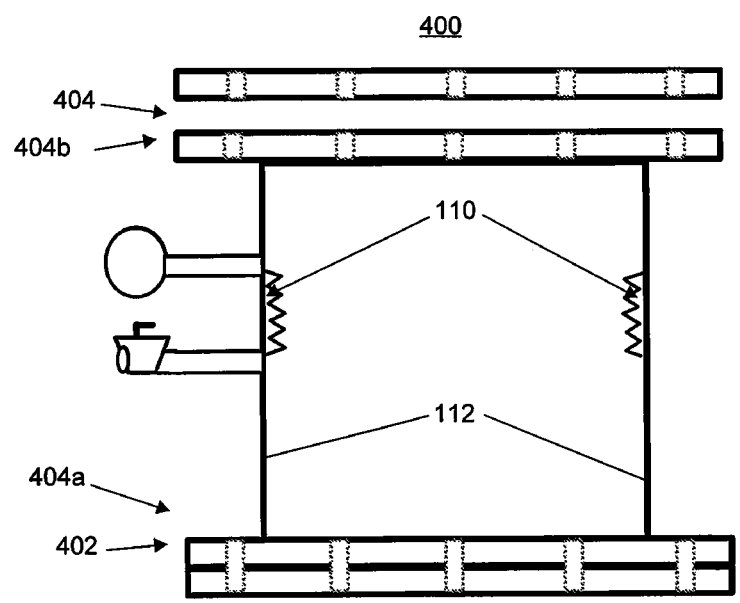
FIG. 4 illustrates a simple tube vessel with ends, temperature control on top and bottom.

Referring now still to FIG. 4, a simple tube vessel 404 with ends 404a and 404b is shown as a design feature of Reflux Rinsing apparatus 400. Temperature control mechanisms are provided on top 404 and bottom 402 of Reflux Rinsing apparatus 400.

Figure 5:
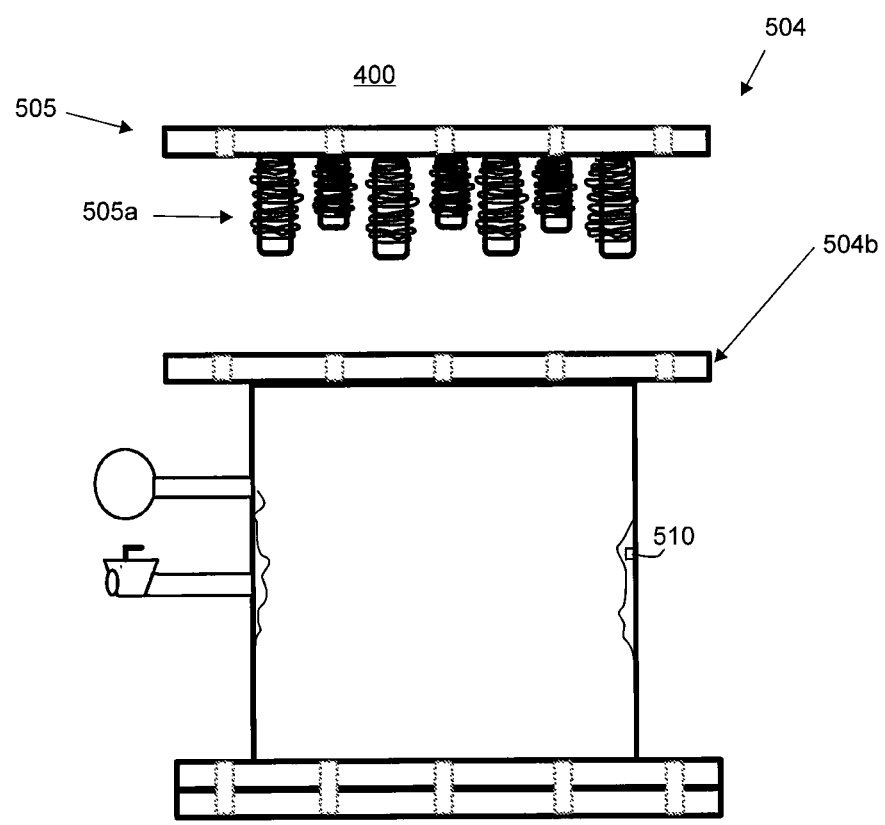
FIG. 5 illustrates a tube vessel with surfaces attached to top.

Referring now to FIG. 5, a tube vessel 504 is provided with lid 505 removably attached by engagement fingers to top 504b and surface area enhancement 505a as a design feature of Reflux Rinsing apparatus 400. Lid 505 facilitates loading, harvesting, and cleaning Reflux Rinsing apparatus 400. Crystalline mass 510 is spread on surfaces of Reflux Rinsing apparatus 400.

Figure 6:
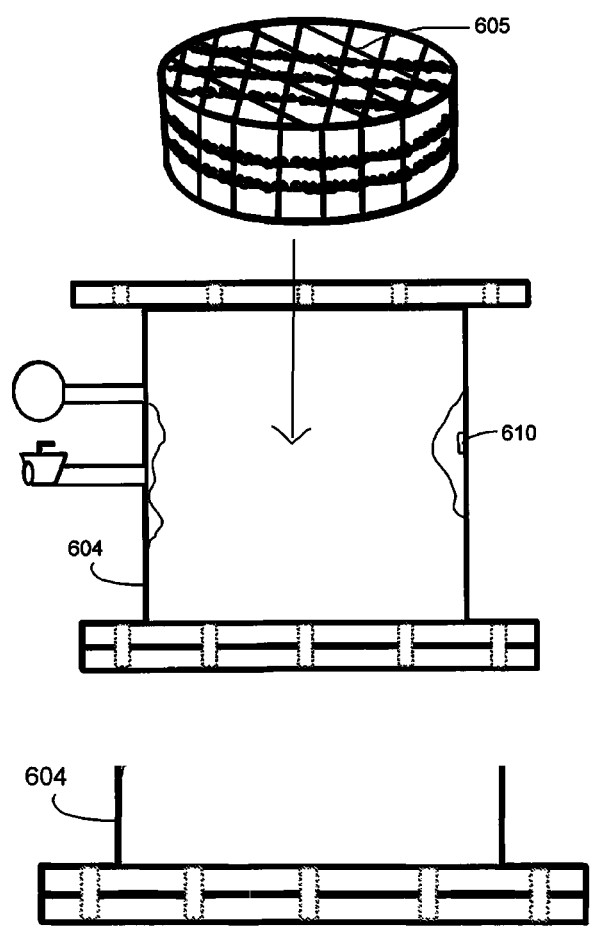
FIG. 6 illustrates a tube with block insert.

Referring now to FIG. 6, a tube vessel 604 with block 605 is inserted into vessel 604 as a design feature of Reflux Rinsing apparatus 400. Block 605 is used to facilitate loading, removing, harvesting, and cleaning Reflux Rinsing apparatus 400. Once again, crystalline mass 610 is spread on the surfaces of Reflux Rinsing apparatus 400.

Figure 7:
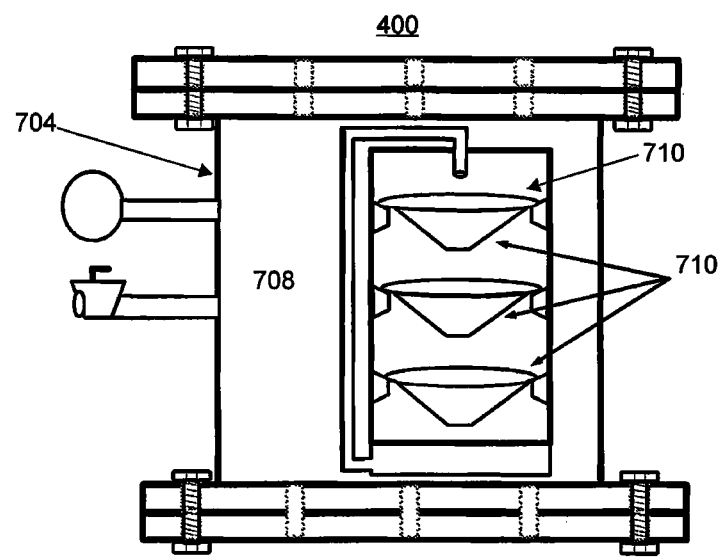
FIG. 7 illustrates a tube with side-arm vapor channel and funnel-shaped Inserts in body of vessel.

Referring now to FIG. 7, a tube vessel 704 is equipped with a side-arm vapor channel 708 and a set of funnel-shaped inserts 710 as a design feature of Reflux Rinsing apparatus 400.

Figure 8:
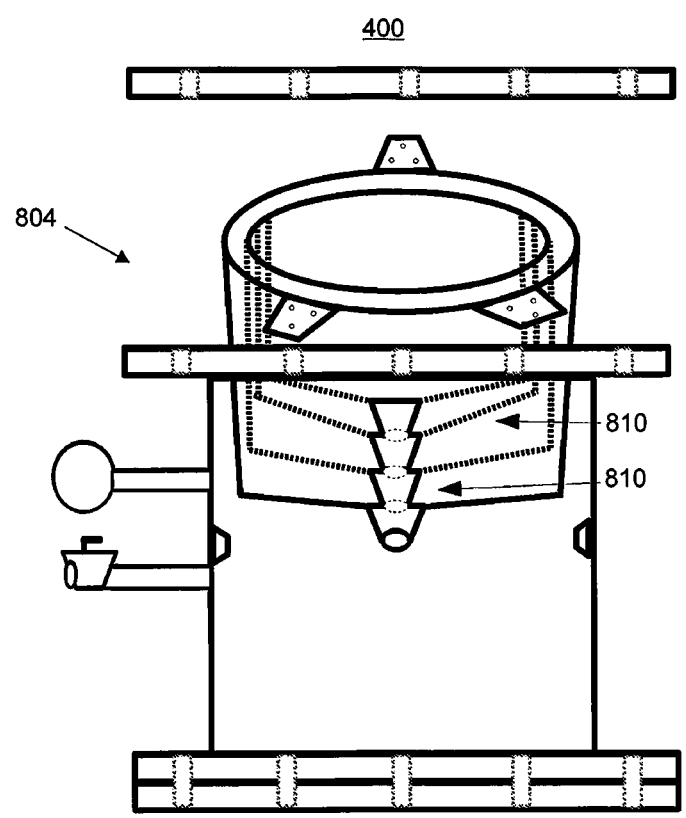
FIG. 8 illustrates nesting funnel inserts in body of vessel.
Figure 9:
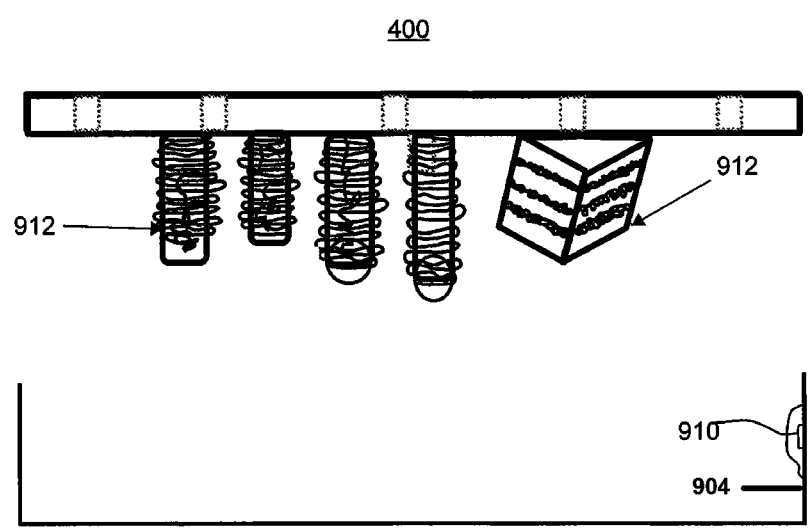
FIG. 9 illustrates nipples, rods and ridges for surface area.
Figure 10:
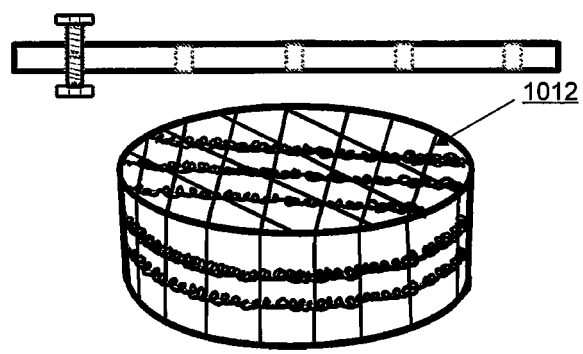
FIG. 10 illustrates a honeycomb insert for surface area.

Referring now to FIG. 8, nesting funnels 810 are inserted in the body of pressure vessel 804 as a design feature of Reflux Rinsing apparatus 400. Once again, crystalline mass 810 is spread on the surfaces of Reflux Rinsing apparatus 400.

Referring now to FIGS. 9-13, various configurations of the interior surfaces of Reflux Rinsing apparatus 400 control the amount of solvent 108 (FIGS. 1-3) in the film covering the crystalline mass 910, the residence time of solvent 108 on crystalline mass 910, and the flow of fresh solvent 108 thereover. The starting crystalline mass 910 can be sprayed, smeared, or added to vessel 904. The slope, length of smear, depth of smear (ribs), flow of impurities, and crystal creep down the walls 412 can be controlled.

Referring now again to FIG. 9, nipples, rods, and ridges 912 are attached to surface areas of Reflux Rinsing apparatus 400 as a design feature thereof. Once again, crystalline mass 910 is spread on the surfaces of Reflux Rinsing apparatus 400.

Referring now again to FIG. 10, a honeycomb 1012 is shown and is insertable into and attachable to surface areas of Reflux Rinsing apparatus 400 (e.g., FIG. 4).

Figure 11:
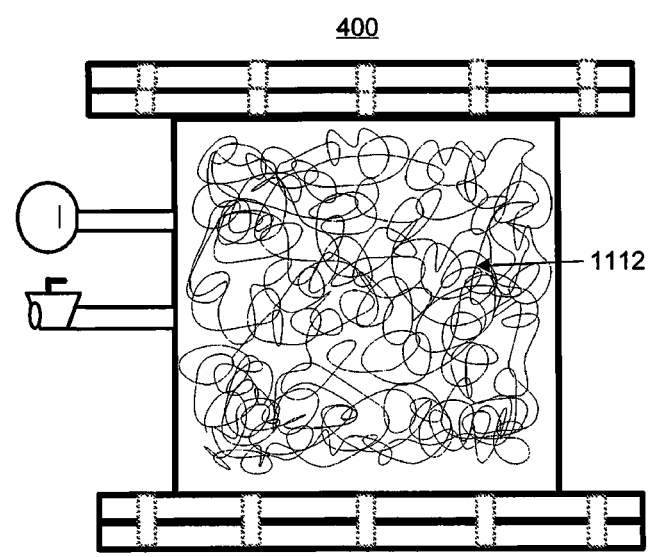
FIG. 11 illustrates a gauze for surface area.

Referring now also to FIG. 11, gauze 1112 is attached to surface areas of Reflux Rinsing apparatus 400 as a design feature thereof.

Figure 12:
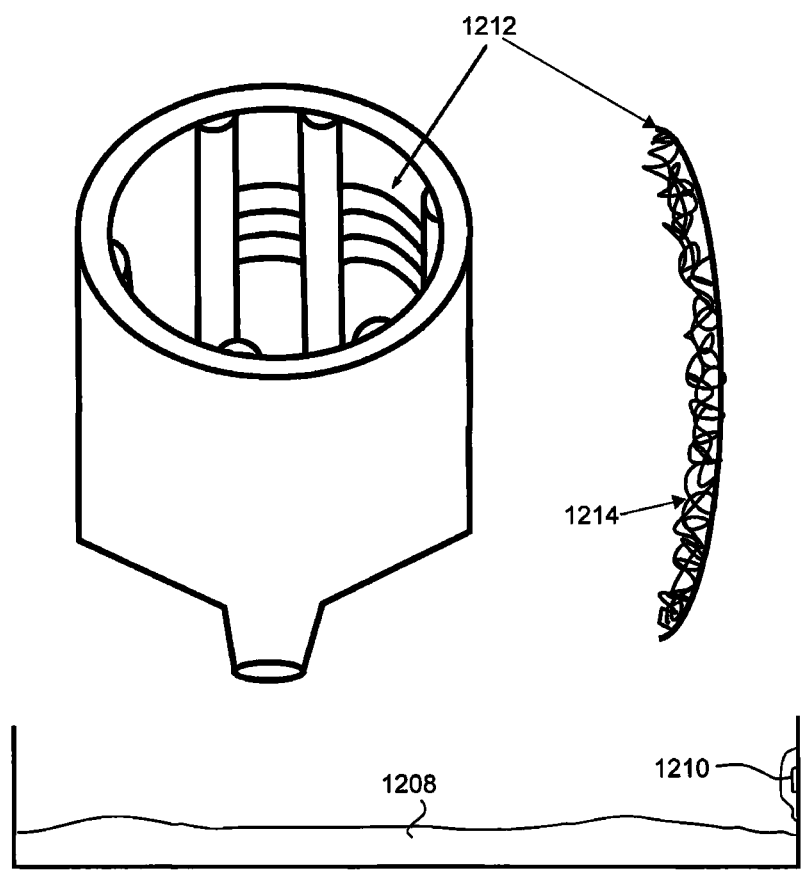
FIG. 12 illustrates ridges for depth of crystal bed and solvent flow, channeling

Referring now also to FIG. 12, ridges 1212 are formed on surface areas of Reflux Rinsing apparatus 400 as a design feature thereof. Ridges 1212 provide depth of the crystal bed 1214 and facilitate channeling flow of solvent 1208. Once again, crystalline mass 1210 is spread on the surfaces of Reflux Rinsing apparatus 400 (e.g., FIG. 4).

Figure 13:
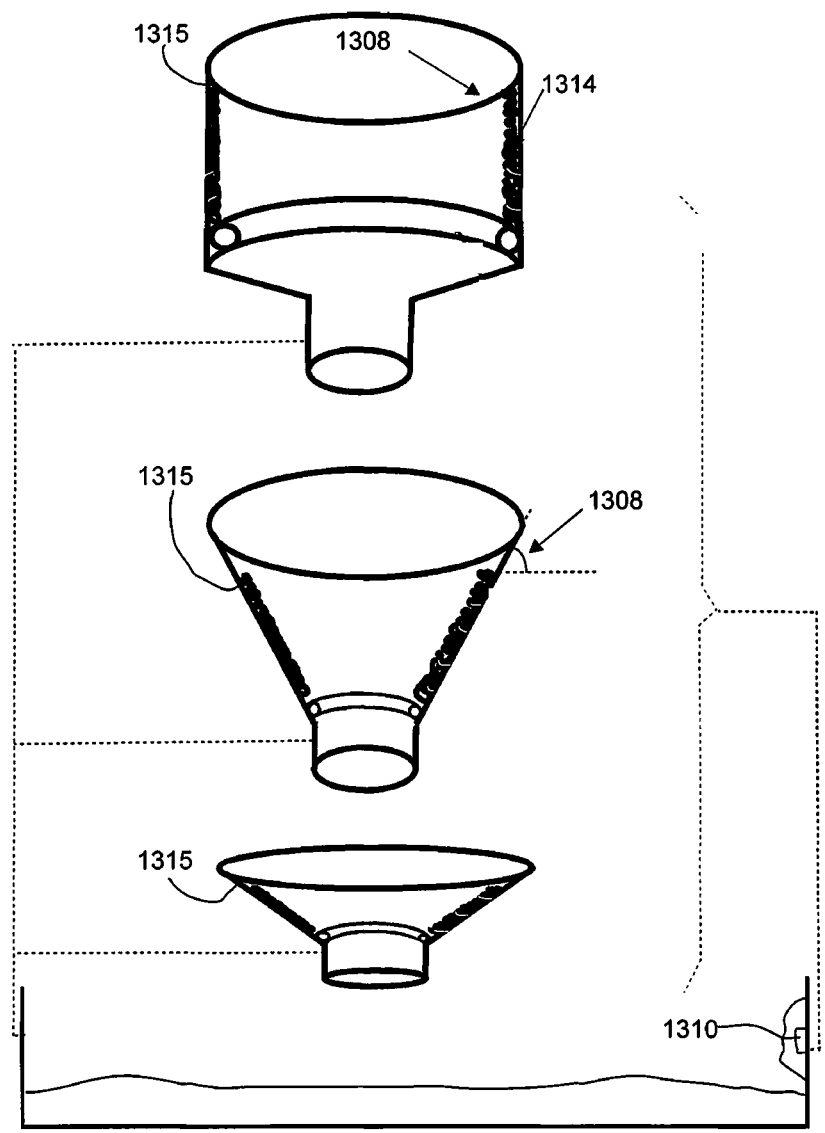
FIG. 13 illustrates controlling flow by angle of crystal bed.

Referring now to FIG. 13, the flow of solvent 1308 over the crystal bed 1314 is controlled by the angle thereof relative to a horizontal plane of Reflux Rinsing apparatus 400 (e.g., FIG. 4). Any mechanism 1315 for adjusting the angle of crystal bed 1314 can be incorporated in Reflux Rinsing apparatus 400 (e.g., FIG. 4). Once again, crystalline mass 1310 is spread on the surfaces of Reflux Rinsing apparatus 400 (e.g., FIG. 4).

Reflux Rinsing apparatus 400 can be modular, making it easy to load and unload, with the ability to add vibration of controlled frequency and to control all variables over multiple cycle times. Moreover, Reflux Rinsing apparatus 400 has design features necessary to prevent disruption of crystalline mass 1310 during solvent addition or removal.

Figure 14:
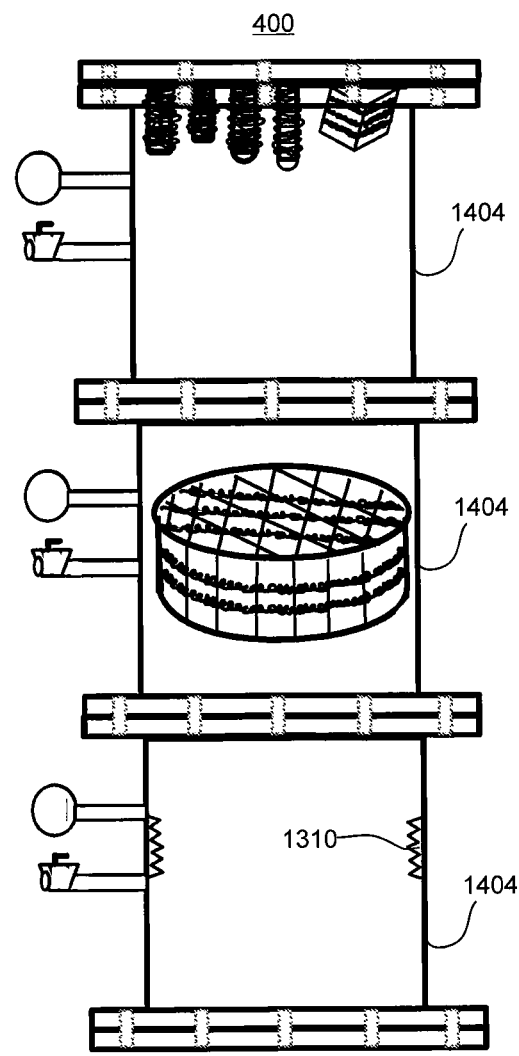
FIG. 14 illustrates a stackable design feature.
Figure 15:
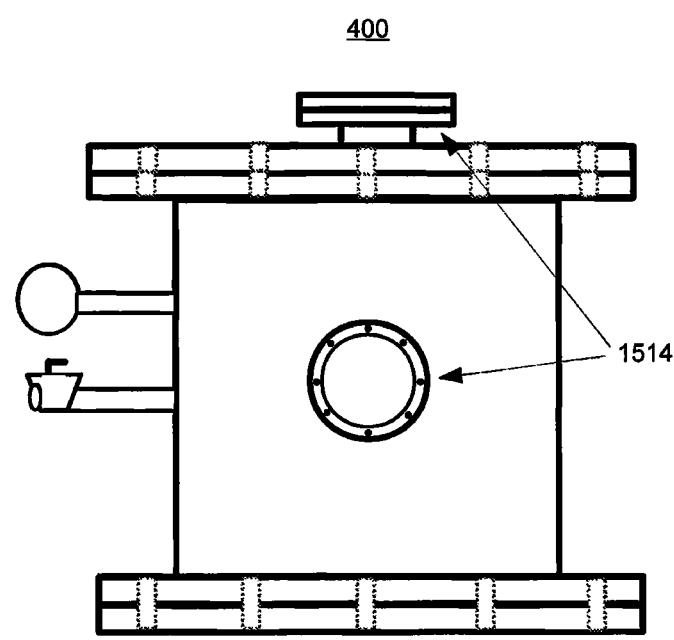
FIG. 15 illustrates a sight glass design feature.
Figure 16:
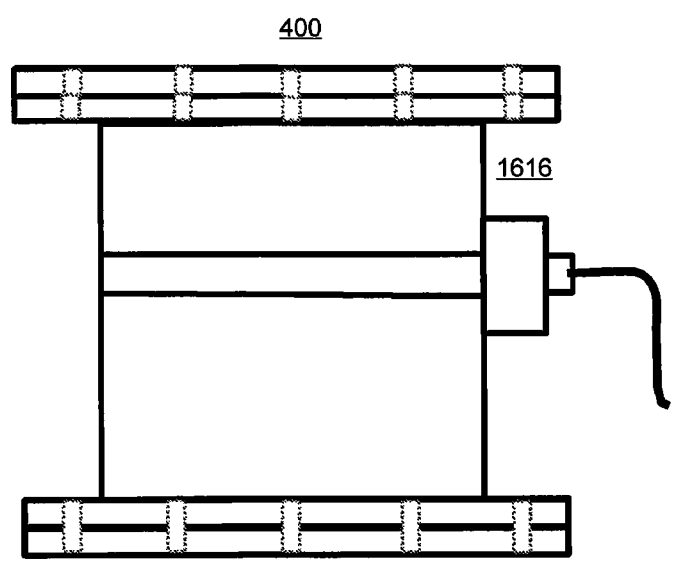
FIG. 16 illustrates a vibration source.

Referring now to FIGS. 14-16, examples of other design features for Reflux Rinsing apparatus 400 are shown.

Referring now again to FIG. 14, a plurality of vessels 1404 can be stacked, as shown, in Reflux Rinsing apparatus 400 as a design feature thereof.

Referring now also to FIG. 15, sight glass 1514 can be placed anywhere on apparatus 400, as shown, as a design feature of Reflux Rinsing apparatus 400.

Referring now also to FIG. 16, a source of vibration 1616 can be operatively connected to Reflux Rinsing apparatus 400 as a design feature thereof.

Figure 17:
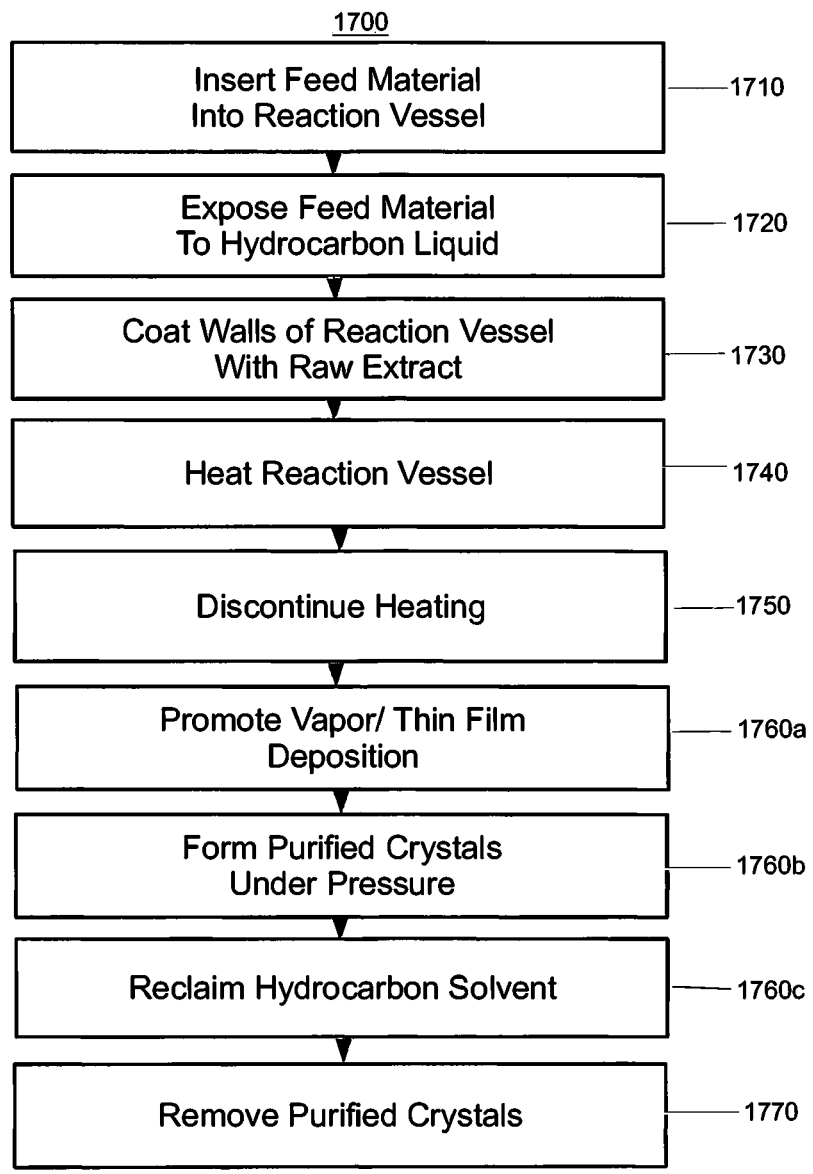
FIG. 17 depicts a flow chart of system operations.

Referring now to FIG. 17, a flow chart of operations 1700 is shown. Flowers and trim of one or more *cannabis* plants are provided, step 1710. The plant material is soaked with a mixture of butane and propane in a reaction or collection vessel, step 1720. The walls and/or bottom surface of the reaction or collection vessel are coated with the material, step 1730.

The collection vessel is heated to a temperature of approximately 115° F., step 1740, after which the heat is no longer applied, step 1750.

The vapor/thin-film DER is promoted, step 1760*a*, forming purified crystals under pressure by allowing the mixture to cool or heat, step 1760*b*, after which the hydrocarbon solvent is reclaimed, step 1760*c*. Thermal cycling, if required, can occur among steps 1740, 1760*a*, and 1760*b*. It has been found that a predetermined range is most efficient for forming crystals, so thermal cycling occurs within the boundary temperatures of the range.

The hydrocarbon solvent is reclaimed from the reaction vessel, step 1760*c*, leaving behind purified crystals, which are scraped from the sides of the reaction or collection vessel once it is opened, step 1770.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

What is claimed is:

1. A method of purifying THC acid using solvent vapor through dynamic equilibrium recrystallization, comprising:
    inserting feed material having THC acid into a vessel;
    exposing the feed material to a hydrocarbon liquid in the vessel to form at least one of a raw extract having THC acid or a suspension containing THC acid crystals;
    heating the vessel and contents therein;
    forming purified crystals of THC acid or further purifying crystals of THC acid on a surface of the vessel; and
    reclaiming a hydrocarbon solvent from the vessel, leaving therein purified crystals of THC acid and impurities.

2. The method according to claim 1, wherein the hydrocarbon liquid includes a mixture of butane and propane.

3. The method according to claim 1, wherein heating the vessel and contents therein includes heating the contents therein under pressure.

4. The method according to claim 3, wherein the hydrocarbon liquid includes a mixture of butane and propane.

5. The method according to claim 4, wherein the pressure is adjustable and is dependent on a butane:propane ratio of the hydrocarbon liquid.

6. The method according to claim 1, wherein the feed material includes at least one of flowers, trim or stems from a plant.

7. The method according to claim 1, wherein the feed material includes THC acid crystals.

8. The method according to claim 1, wherein heating the vessel and contents therein includes heating at least one of the vessel or the contents therein to 115° F.

9. The method according to claim 1, wherein the vessel includes structure configured to increase surface area therein.

10. The method according to claim 9, wherein forming purified crystals of THC acid or further purifying crystals of THC acid on a portion of the vessel includes at least one of forming purified crystals of THC acid or further purifying crystals of THC acid on the structure of the vessel.

11. The method according to claim 1, further including opening the vessel and removing the purified crystals of THC acid and impurities therefrom.

12. The method according to claim 11, wherein opening the vessel and removing the purified crystals of THC acid and impurities therefrom includes scraping the purified crystals of THC acid from the surface of the vessel.

13. The method according to claim 1, further including discontinuing heating the vessel and contents therein.

14. The method according to claim 13, further including repeating heating the vessel and contents therein, and repeating discontinuing heating the vessel and contents therein.

15. The method according to claim 1, further including cooling the contents of the vessel.

16. The method according to claim 1, wherein the hydrocarbon liquid includes at least one of butane or propane.

* * * * *